United States Patent
Narimatsu

(10) Patent No.: US 6,186,954 B1
(45) Date of Patent: Feb. 13, 2001

(54) BLOOD-PRESSURE MONITORING APPARATUS

(75) Inventor: Kiyoyuki Narimatsu, Kasugai (JP)

(73) Assignee: Colin Corporation, Komaki (JP)

(*) Notice: Under 35 U.S.C. 154(b), the term of this patent shall be extended for 0 days.

(21) Appl. No.: 09/397,637

(22) Filed: Sep. 16, 1999

(30) Foreign Application Priority Data

Oct. 14, 1998 (JP) .................................................. 10-291964

(51) Int. Cl.$^7$ ...................................................... A61B 5/00
(52) U.S. Cl. .......................... 600/490; 600/485; 600/494; 600/500; 600/520
(58) Field of Search ................................... 600/483–485, 600/490, 492–495, 500–502, 520

(56) References Cited

U.S. PATENT DOCUMENTS

| | | | |
|---|---|---|---|
| 5,906,581 | * | 5/1999 | Tsuda ...................................... 600/490 |
| 6,036,651 | * | 3/2000 | Inukai et al. ........................... 600/485 |

* cited by examiner

Primary Examiner—Cary O'Connor
Assistant Examiner—Ryan Carter
(74) Attorney, Agent, or Firm—Oliff & Berridge, PLC

(57) ABSTRACT

A blood-pressure monitoring apparatus including a measuring device which includes an inflatable cuff adapted to apply a pressing pressure to a body portion of a living subject and measures a blood-pressure value of the living subject by changing the pressing pressure of the inflatable cuff, an information obtaining device which iteratively obtains a piece of information relating to propagation of a pulse wave through an arterial vessel of the subject, an estimating device for iteratively estimating a blood-pressure value, EBP, of the subject, based on each piece of pulse-wave-propagation-relating information, PWPI, obtained by the information obtaining device, according to a linear relationship between pulse-wave-propagation-relating information and blood pressure, the linear relationship being defined by a linear expression, EBP=$\alpha$(PWPI)+$\alpha$, where $\alpha$ is a slope and $\beta$ is an intercept, an index-value calculating device for calculating an index value indicative of a hardness of a blood vessel of the subject, and a slope determining device for determining, based on the calculated index value, the slope $\alpha$ of the linear expression.

16 Claims, 9 Drawing Sheets

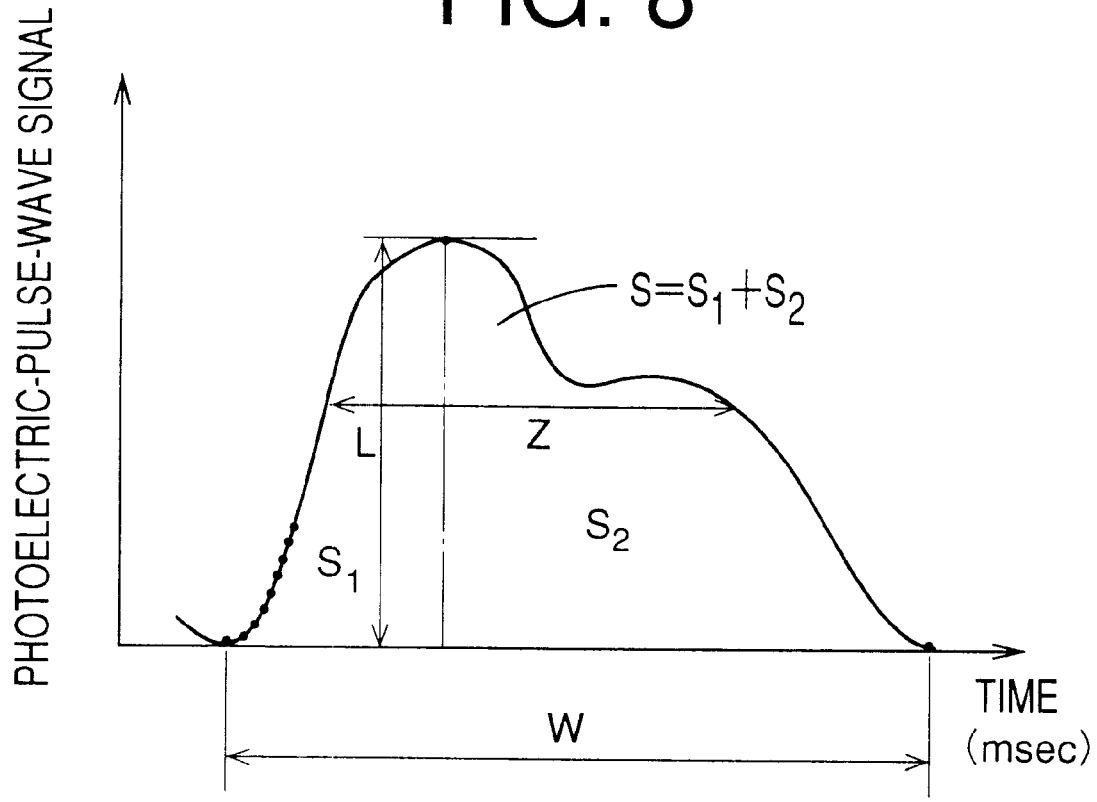

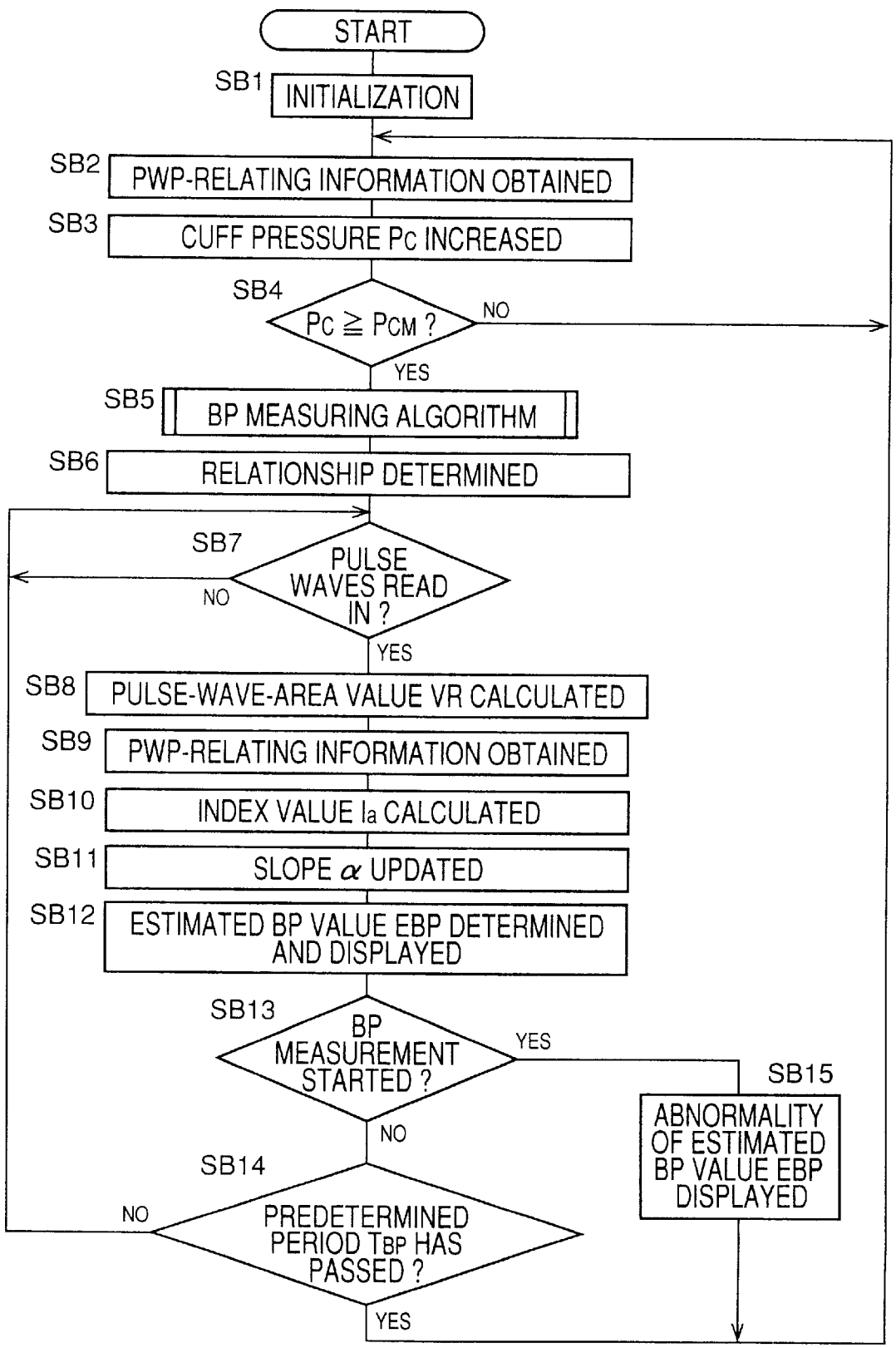

BLOOD-PRESSURE MONITORING APPARATUS

BACKGROUND OF THE INVENTION

1. Field of the Invention

The present invention relates to a blood-pressure monitoring apparatus which monitors a blood pressure of a living subject based on information relating to propagation of a pulse wave through an arterial vessel of the subject.

2. Related Art Statement

As information relating to a pulse wave which propagates through an arterial vessel of a living subject, there are known a pulse-wave-propagation time DT and a pulse-wave-propagation velocity $V_M$ (m/s). The pulse-wave-propagation time DT is a time which is needed by a pulse wave to propagate between two different positions of the arterial vessel. Additionally, it is known that the above pulse-wave-propagation-relating information is, within a predetermined range, substantially proportional to the blood pressure ("BP", mmHg) of the living subject. Therefore, there has been proposed a BP monitoring apparatus which determines, in advance, coefficients $\alpha$, $\beta$ in the following expression: EBP=$\alpha$(DT)+$\beta$ (where $\alpha$ is a negative constant and $\beta$ is a positive constant), or EBP=$\alpha$($V_M$)+$\beta$ (where $\alpha$ and $\beta$ are positive constants), based on two measured BP values of the subject and two measured pulse-wave-propagation time values (DT) or two measured pulse-wave-propagation velocity values ($V_M$), iteratively determines an estimated BP value EBP of the subject, based on each piece of subsequently obtained pulse-wave-propagation-relating information, according to the above-indicated first or second expression, and starts a BP measurement using an inflatable cuff when an estimated BP value EBP is judged as being abnormal.

Meanwhile, at least two measured BP values and at least two pieces of obtained pulse-wave-propagation-relating information are needed for determining a relationship between pulse-wave-propagation-relating information and estimated BP value EBP represented by the first or second expression, because each of the first and second expressions includes two unknown constants. In order to determine an accurate relationship, it is desirable that the two measured BP values have the greatest possible difference. However, the conventional BP monitoring device carries out the second BP measuring operation using the inflatable cuff, irrespective of what BP value the subject currently has. Accordingly, the accuracy of the determined relationship may be insufficient. If many BP measuring operations each using the cuff are repeated till two BP values having a sufficiently great difference are obtained, it takes a long time and results in giving an unnecessary load to the subject.

SUMMERY OF THE INVENTION

It is therefore an object of the present invention to provide a blood-pressure monitoring apparatus which determines an estimated blood-pressure value of a living subject based on information relating to propagation of a pulse wave through an arterial vessel of the subject and which accurately and efficiently determines a relationship between pulse-wave-propagation-relating information and estimated blood-pressure value.

The Inventor has carried out various studies and has found that as a blood vessel of a living subject becomes harder, the velocity of a pulse wave which propagates through the blood vessel becomes faster and that as the blood vessel becomes softer, the velocity becomes slower. That is, the Inventor has found that the slope of a linear relationship between pulse-wave-propagation-relating information and estimated BP value EBP is proportional to the hardness of the blood vessel. The present invention has been developed based on this finding, and is directed to the art of determining the slope of the linear relationship based on the hardness of the blood vessel.

The present invention provides a blood-pressure monitoring apparatus which has one or more of the technical features that are described below in respective paragraphs given parenthesized sequential numbers (1) to (16). Any technical feature which includes another technical feature shall do so by referring, at the beginning, to the parenthesized sequential number given to that technical feature.

(1) According to a first feature of the present invention, there is provided a blood-pressure monitoring apparatus comprising a measuring device which includes an inflatable cuff adapted to apply a pressing pressure to a body portion of a living subject and which measures at least one blood-pressure value of the living subject by changing the pressing pressure of the inflatable cuff, a pulse-wave-propagation-relating-information obtaining device which iteratively obtains a piece of pulse-wave-propagation-relating information relating to propagation of a pulse wave through an arterial vessel of the living subject, estimating means for iteratively estimating a blood-pressure value, EBP, of the living subject, based on each piece of pulse-wave-propagation-relating information, PWPI, obtained by the pulse-wave-propagation-relating-information obtaining device, according to a linear relationship between pulse-wave-propagation-relating information and blood pressure, the linear relationship being defined by a following linear expression, EBP=$\alpha$(PWPI)+$\beta$, where $\alpha$ is a slope and $\beta$ is an intercept; index-value calculating means for calculating, based on the blood-pressure value of the living subject measured by the measuring device, an index value indicative of a hardness of a blood vessel of the living subject, slope determining means for determining, based on the calculated index value, the slope $\alpha$ of the linear expression, and intercept determining means for determining the intercept $\beta$ of the linear expression, based on the blood-pressure value measured by the measuring device, the piece of pulse-wave-propagation-relating information obtained by the pulse-wave-propagation-relating-information obtaining device when the blood-pressure value is measured by the measuring device, and the slope $\alpha$ determined by the slope determining means. The present BP monitoring apparatus can determine a relationship between pulse-wave-propagation-relating information and (estimated) blood pressure, based on a single measured BP value and a single piece of obtained pulse-wave-propagation-relating information.

(2) According to a second feature of the present invention, there is provided a blood-pressure monitoring apparatus comprising a measuring device which includes an inflatable cuff adapted to apply a pressing pressure to a first body portion of a living subject and which measures at least one blood-pressure value of the living subject by changing the pressing pressure of the inflatable cuff, a pulse-wave-propagation-relating-information obtaining device which iteratively obtains a piece of pulse-wave-propagation-relating information relating to propagation of a pulse wave through an arterial vessel of the living subject, estimating means for iteratively estimating a blood-pressure value, EBP, of the living subject, based on each piece of pulse-wave-propagation-relating information, PWPI, obtained by the pulse-wave-propagation-relating-information obtaining device, according to a linear relationship between pulse-wave-propagation-relating information and blood pressure, the linear relationship being defined by a following linear expression, $EBP=\alpha(PWPI)+\beta$, where $\alpha$ is a slope and $\beta$ is an intercept, a pulse-wave detecting device which detects a peripheral pulse wave including a plurality of heartbeat-synchronous pulses, from a second body portion of the living subject, peripheral-pulse-wave-relating-value calculating means for iteratively calculating a peripheral-pulse-wave-relating value relating to each of the heartbeat-synchronous pulses of the peripheral pulse wave detected by the pulse-wave detecting device, index-value calculating means for iteratively calculating, based on each of the iteratively calculated peripheral-pulse-wave-relating values, an index value indicative of a hardness of a blood vessel of the living subject, and slope updating means for iteratively determining, based on each of the iteratively calculated index values, a new slope $\alpha$ for the linear expression, and updating a current slope $\alpha$ of the linear expression by replacing the current slope $\alpha$ with the determined new slope $\alpha$. The present BP monitoring apparatus can enjoy improved accuracy of the relationship between pulse-wave-propagation-relating information and (estimated) blood pressure.

(3) According to a third feature of the present invention, there is provided a blood-pressure monitoring apparatus comprising a measuring device which includes an inflatable cuff adapted to apply a pressing pressure to a first body portion of a living subject and which measures at least one blood-pressure value of the living subject by changing the pressing pressure of the inflatable cuff, a pulse-wave-propagation-relating-information obtaining device which iteratively obtains a piece of pulse-wave-propagation-relating information relating to propagation of a pulse wave through an arterial vessel of the living subject, estimating means for iteratively estimating a blood-pressure value, EBP, of the living subject, based on each piece of pulse-wave-propagation-relating information, PWPI, obtained by the pulse-wave-propagation-relating-information obtaining device, according to a linear relationship between pulse-wave-propagation-relating information and blood pressure, the linear relationship being defined by a following linear expression, $EBP=\alpha(PWPI)+\beta$, where $\alpha$ is a slope and $\beta$ is an intercept, index-value calculating means for calculating an index value indicative of a hardness of a blood vessel of the living subject, and slope determining means for determining, based on the calculated index value, the slope $\alpha$ of the linear expression. The present BP monitoring apparatus can determine the slope of the linear relationship between pulse-wave-propagation-relating information and (estimated) blood pressure, based on the hardness of the blood vessel of the subject.

(4) According to a fourth feature of the present invention that includes the third feature (3), the index-value calculating means comprises means for calculating, based on the blood-pressure value of the living subject measured by the measuring device, the index value indicative of the hardness of the blood vessel of the living subject.

(5) According to a fifth feature of the present invention that includes the third or fourth feature (3) or (4), the monitoring apparatus further comprises intercept determining means for determining the intercept $\beta$ of the linear expression, based on the blood-pressure value measured by the measuring device, the piece of pulse-wave-propagation-relating information obtained by the pulse-wave-propagation-relating-information obtaining device when the blood-pressure value is measured by the measuring device, and the slope $\alpha$ determined by the slope determining means.

(6) According to a sixth feature of the present invention that includes any one of the third to fifth features (3) to (5), the monitoring apparatus further comprises a pulse-wave detecting device which detects a peripheral pulse wave including a plurality of heartbeat-synchronous pulses, from a second body portion of the living subject, and peripheral-pulse-wave-relating-value calculating means for iteratively calculating a peripheral-pulse-wave-relating value relating to each of the heartbeat-synchronous pulses of the peripheral pulse wave detected by the pulse-wave detecting device, and the index-value calculating means comprises means for iteratively calculating, based on each of the iteratively calculated peripheral-pulse-wave-relating values, the index value indicative of the hardness of the blood vessel of the living subject.

(7) According to a seventh feature of the present invention that includes any one of the third to fifth features (3) to (5), the slope determining means comprises slope updating means for iteratively determining a new slope $\alpha$ for the linear expression, based on each of the iteratively calculated index values, and updating a current slope $\alpha$ of the linear expression by replacing the current slope $\alpha$ with the determined new slope $\alpha$.

(8) According to an eighth feature of the present invention that includes the fourth feature (4), the monitoring apparatus further comprising intercept determining means for determining the intercept $\beta$ of the linear expression, based on the blood-pressure value measured by the measuring device, the piece of pulse-wave-propagation-relating information obtained by the pulse-wave-propagation-relating-information obtaining device when the blood-pressure value is measured by the measuring device, and the slope $\alpha$ determined by the slope determining means, a pulse-wave detecting device which detects a peripheral pulse wave including a plurality of heartbeat-synchronous pulses, from a second body portion of the living subject, peripheral-pulse-wave-relating-value calculating means for iteratively calculating a peripheral-pulse-wave-relating value relating to each of the heartbeat-synchronous pulses of the peripheral pulse wave detected by the pulse-wave detecting device, the index-value calculating means comprising means for iteratively calculating, based on each of the iteratively calculated peripheral-pulse-wave-relating values, the index value indicative of the hardness of the blood vessel of the living subject, and the slope determining means comprising slope updating means for iteratively determining a new slope $\alpha$ for the linear expression, based on each of the iteratively calculated index values, and updating a current slope $\alpha$ of the linear expression by replacing the current slope $\alpha$ with the determined new slope $\alpha$.

(9) According to a ninth feature of the present invention that includes any one of the third to eighth features (3) to (8), the pulse-wave-propagation-relating-information obtaining device comprises at least one of pulse-wave-propagation-time calculating means for iteratively calculating a pulse-wave propagation time which is needed for each of a plurality of heartbeat-synchronous pulses of the pulse wave to propagate between two portions of the arterial vessel of the living subject, and pulse-wave-propagation-velocity calculating means for iteratively calculating a pulse-wave propagation velocity at which each of a plurality of heartbeat-synchronous pulses of the pulse wave propagates between two portions of the arterial vessel of the living subject.

(10) According to a tenth feature of the present invention that includes any one of the third to ninth features (3) to (9), the pulse-wave-propagation-relating-information obtaining device comprises an electrocardiographic-pulse-wave detecting device which includes a plurality of electrodes adapted to be put on a plurality of portions of the living body and detects an electrocardiographic pulse wave including a plurality of heartbeat-synchronous pulses, from the subject via the electrodes, and a photoelectric-pulse-wave detecting device which is adapted to be worn on a second body portion of the living subject, and which emits a light toward the second body portion and obtains a photoelectric pulse wave including a plurality of heartbeat-synchronous pulses, from the light received from the second body portion.

(11) According to an eleventh feature of the present invention that includes any one of the third to tenth features (3) to (10), the measuring device comprises means for measuring a systolic, a mean, and a diastolic blood-pressure value of the living subject by changing the pressing pressure of the inflatable cuff, and the index-value calculating means comprises means for calculating a pulse pressure by subtracting the measured diastolic blood-pressure value from the measured systolic blood-pressure value, and calculating the index value by dividing the thus calculated pulse pressure by the measured mean blood-pressure value.

(12) According to a twelfth feature of the present invention that includes any one of the third to tenth features (3) to (10), the index-value calculating means comprises means for calculating the index value based on the blood-pressure value measured by the measuring device and the piece of pulse-wave-propagation-relating information obtained by the pulse-wave-propagation-relating-information obtaining device when the blood-pressure value is measured by the measuring device.

(13) According to a thirteenth feature of the present invention that includes any one of the sixth to tenth features (6) to (12), the index-value calculating means comprises means for iteratively calculating the index value based on each piece of pulse-wave-propagation-relating information iteratively obtained by the pulse-wave-propagation-relating-information obtaining device and the each peripheral-pulse-wave-relating value iteratively calculated by the peripheral-pulse-wave-relating-value calculating means.

(14) According to a thirteenth feature of the present invention that includes any one of the sixth to tenth features (6) to (13), the peripheral-pulse-wave-relating-value calculating means comprises means for iteratively calculating a value relating to an area defined by a waveform of the each heartbeat-synchronous pulse of the peripheral pulse wave detected by the pulse-wave detecting device.

(15) According to a thirteenth feature of the present invention that includes any one of the third to fourteenth features (3) to (14), the slope determining means comprises means for determining the slope α of the linear expression based on the calculated index value, $I_a$, according to a following expression: $\alpha = k \times I_a + c$, where k and c are predetermined constants.

(16) According to a sixteenth feature of the present invention that includes any one of the third to fifteenth features (3) to (15), the monitoring apparatus further comprises starting means for judging whether the blood-pressure value estimated by the estimating means is abnormal, and staring a blood-pressure measurement of the measuring device when the estimated blood-pressure value is judged as being abnormal.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 8 is a view for illustrating the manner in which a normalized pulse-wave area value VR is calculated by an operation of the control device of the apparatus of FIG. 7; and FIG. 9 is a flow chart corresponding to FIG. 6, for representing a control program according to which the control device of the apparatus of FIG. 7 is operated for monitoring the BP of a living subject.

DETAILED DESCRIPTION OF THE PREFERRED EMBODIMENTS

Figure 1:
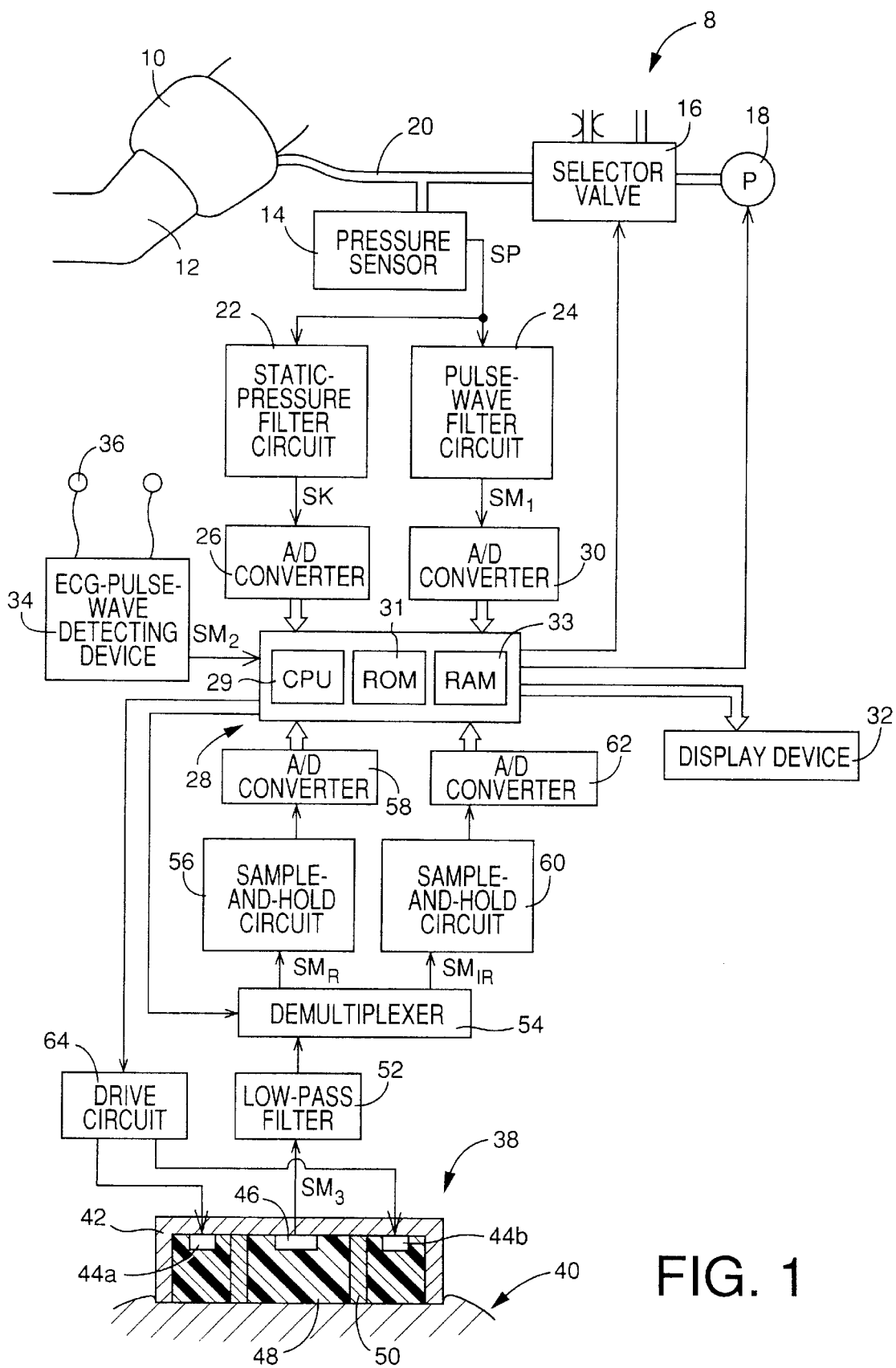
FIG. 1 is a diagrammatic view of a blood-pressure ("BP") monitoring apparatus embodying the present invention.

Referring to FIG. 1, there will be described a blood-pressure ("BP") monitoring apparatus 8 embodying the present invention.

In FIG. 1, the BP monitoring apparatus 8 includes an inflatable cuff 10 which has a belt-like cloth bag and a rubber bag accommodated in the cloth bag and which is adapted to be wrapped around, e.g., a right upper arm 12 of a patient as a living subject, and a pressure sensor 14, a selector valve 16 and an air pump 18 each of which is connected to the cuff 10 via piping 20. The selector valve 16 is selectively placed in an inflation position in which the selector valve 16 permits a pressurized air to be supplied from the air pump 18 to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the inflatable cuff 10, and supplies a pressure signal SP representative of the detected pressure to each of a static-pressure filter circuit 22 and a pulse-wave filter circuit 24. The static-pressure filter circuit 22 includes a low-pass filter and extracts, from the pressure signal SP, a static component contained in the signal SP, i.e., cuff-pressure signal SK representative of the static cuff pressure. The cuff-pressure signal SK is supplied to an electronic control device 28 via an analog-to-digital ("A/D") converter 26. The pulse-wave filter circuit 24 includes a band-pass filter and extracts, from the pressure signal SP, an oscillatory component having predetermined frequencies, i.e., cuff-pulse-wave signal $SM_1$. The cuff-pulse-wave signal $SM_1$ is supplied to the control device 28 via an A/D converter 30. The cuff-pulse-wave signal $SM_1$ is representative of the cuff pulse wave, i.e., oscillatory pressure wave which is produced from a brachial artery (not shown) of the patient in synchronism with the heartbeat of the patient and is propagated to the inflatable cuff 10.

The control device 28 is provided by a so-called microcomputer including a central processing unit ("CPU") 29, a read only memory ("ROM") 31, a random access memory ("RAM") 33, and an input-and-output ("I/O") port (not shown). The CPU 29 processes signals according to control programs pre-stored in the ROM 31 by utilizing a temporary-storage function of the RAM 33, and supplies drive signals to the selector valve 16 and the air pump 18 through the I/O port.

The BP monitoring apparatus 8 further includes an electrocardiographic (ECG) pulse wave detecting device 34 which continuously detects an ECG pulse wave representative of the action potential of cardiac muscle of the patient, through a plurality of electrodes 36 being put on predetermined body portions of the patient, and supplies an ECG-pulse-wave signal $SM_2$ representative of the detected ECG pulse wave, to the control device 28. The ECG-pulse-wave detecting device 34 is used for detecting a Q-wave or an R-wave of the waveform of each heartbeat-synchronous pulse of the ECG pulse wave that corresponds to a time point when the outputting of blood from the heart of the patient toward the aorta is started. Thus, the ECG-pulse-wave detecting device 34 functions as a first pulse-wave detecting device.

The BP monitoring apparatus 8 further includes a photoelectric-pulse-wave detecting probe 38 (hereinafter, referred to as the "probe" 38) which is employed as part of a pulse oximeter. The probe 38 functions as a second pulse-wave detecting device, or a peripheral-pulse-wave detecting device for detecting a peripheral pulse wave propagated to a peripheral artery including capillaries. The probe 38 is set on a skin or a body surface 40 of the patient, e.g., an end portion of a finger of a left hand of the patient with the help of a band (not shown), such that the probe 38 is held in close contact with the body surface 40. The probe 38 is worn on the hand of one arm different from the other arm around which the cuff 10 is wrapped.

The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements in the case where the first and second groups of light emitting elements 44a, 44b need not be discriminated from each other), a light receiving element 46, such as a photodiode or a phototransister, which is disposed on a central portion of the inner bottom surface of the housing 42, a transparent resin 48 which is integrally disposed in the housing 42 to cover the light emitting elements 44 and the light receiving element 46, and an annular shading member 50 which is disposed between the light emitting elements 44 and the light receiving element 46, for preventing the light receiving element 46 from receiving the lights emitted toward the body surface 40 by the light emitting elements 44 and directly reflected from the body surface 40.

The first group of light emitting elements 44a emit a first light having a first wavelength whose absorbance changes depending on a blood oxygen saturation value of the patient. The first elements 44a emit, e.g., a red light having about 660 nm wavelength. The second group of light emitting elements 44b emit a second light having a second wavelength whose absorbance does not change depending on the blood oxygen saturation value of the patient. The second elements 44b emit, e.g., an infrared light having about 800 nm wavelength. The first and second light emitting elements 44a, 44b alternately emit the red and infrared lights, respectively, at a predetermined frequency, e.g., a relatively high frequency of several hundred Hz to several thousand Hz. The lights emitted toward the body surface 40 by the light emitting elements 44 are reflected from a body tissue of the patient where a dense capillaries occur, and the reflected lights are received by the common light receiving element 46. In place of the 660 nm and 800 nm lights, the first and second light emitting elements 44a, 44b may employ various pairs of lights each pair of which have different wavelengths, so long as one light of each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is reflected by each of the two sorts of hemoglobin.

The light receiving element 46 outputs, through a low-pass filter 52, a photoelectric-pulse-wave signal $SM_3$ representative of an amount of the first or second light received from the body tissue of the patient. The light receiving element 46 is connected to the low-pass filter 52 via an amplifier or the like. The low-pass filter 52 removes, from the photoelectric-pulse-wave signal $SM_3$ input thereto, noise having frequencies higher than that of a pulse wave, and outputs the noise-free signal $SM_3$, to a demultiplexer 54. The photoelectric-pulse-wave signal $SM_3$ is representative of a photoelectric pulse wave which is produced in synchronism with the pulse of the patient.

The demultiplexer 54 is switched according to signals supplied thereto from the control device 28 in synchronism with the alternate light emissions of the first and second light emitting elements 44a, 44b. Thus, the demultiplexer 54 separates the photoelectric-pulse-wave ("PPW") signal SM3 into two PPW signals which correspond to the first and second lights, respectively. More specifically described, the demultiplexer 54 successively supplies, to the I/O port (not shown) of the control device 28, a first PPW signal $SM_R$ representative of the red light having the first wavelength through a first sample-and-hold circuit 56 and an A/D converter 58, and a second PPW signal $SM_{IR}$ representative of the infrared light having the second wavelength through a second sample-and-hold circuit 60 and an A/D converter 62. The first and second sample-and-hold circuits 56, 60 hold the first and second PPW signals $SM_R$, $SM_{IR}$ input thereto, respectively, and do not output the current signals $SM_R$, $SM_{IR}$ to the A/D converters 58, 62, before the prior signals $SM_R$, $SM_{IR}$ are completely converted by the A/D converters 58, 62, respectively.

In the control device 28, the CPU 29 carries out a measuring operation according to control programs pre-stored in the ROM 31 by utilizing the temporary-storage function of the RAM 33. More specifically described, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined duration. In synchronism with the alternate light emissions of the first and second light emitting elements 44a, 44b, the CPU 29 generates a switch signal SC to the demultiplexer 54 to switch the demultiplexer 54 between its first and second positions. Thus, the PPW signal $SM_3$ is separated by the demultiplexer 54 such that the first PPW signal $SM_R$ is supplied to the first sample-and-hold circuit 56 while the second PPW signal $SM_{IR}$ is supplied to the second sample-and-hold circuit 60.

Figure 2:
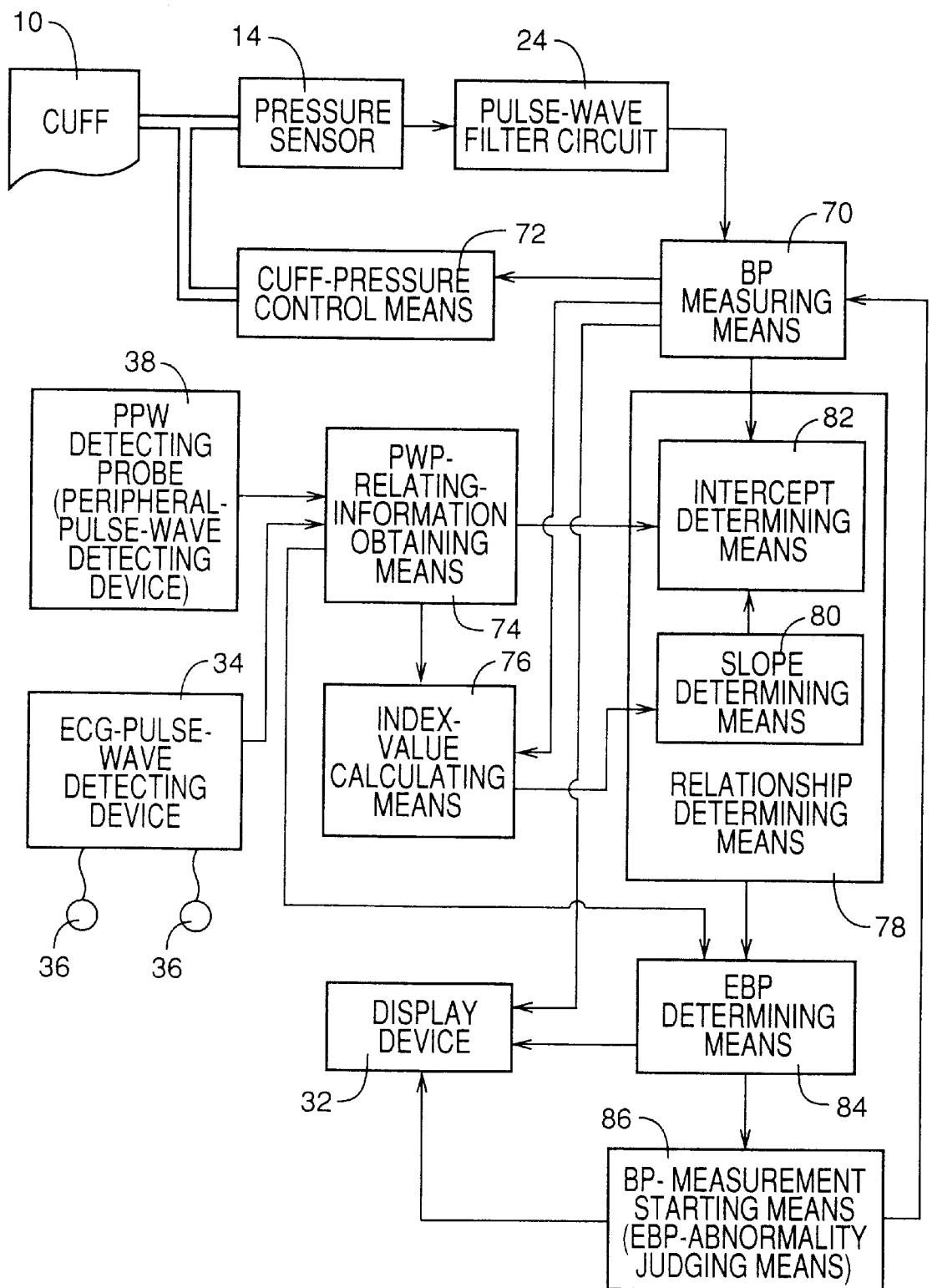
FIG. 2 is a block diagram for illustrating essential functions of an electronic control device of the apparatus of FIG. 1.

FIG. 2 illustrates essential functions of the control device 28 of the present BP monitoring apparatus 8. In the figure, a BP measuring means or circuit 70 measures a systolic, a mean, and a diastolic BP value $BP_{SYS}$, $BP_{MEAN}$, $BP_{DIA}$ of the patient, according to a well known oscillometric method, based on variation of respective amplitudes of heartbeat-synchronous pulses of the pulse wave represented by the cuff-pulse-wave signal $SM_1$ obtained while the cuff pressure which is quickly increased by a cuff-pressure control means or circuit 72 to a target pressure value $P_{CM}$ (e.g., 180 mmHg), is slowly decreased at a predetermined rate, e.g., the rate of about 3 mmHg/sec.

Figure 3:
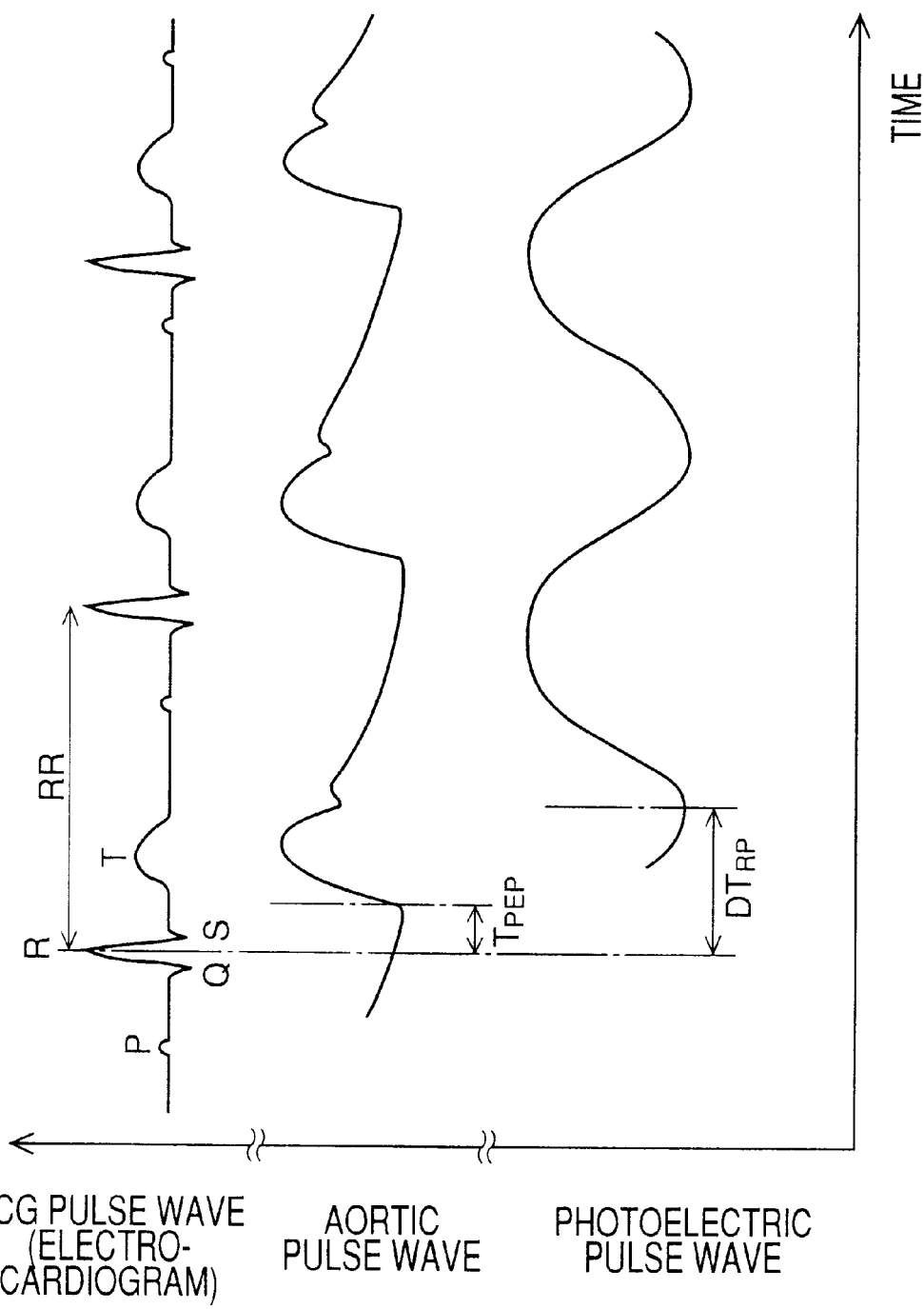
FIG. 3 is a view for illustrating a pulse-wave-propagation time value $DT_{RP}$ obtained by an operation of the control device of the apparatus of FIG. 1.

A pulse wave propagation ("PWP") relating information obtaining means or circuit 74 includes a time-difference calculating means or circuit which iteratively calculates, as a PWP time $DT_{RP}$, a time difference between a predetermined point (e.g., R-wave) on the waveform of each of periodic pulses of the ECG pulse wave that are detected by the ECG-pulse-wave detecting device 34 and a predetermined point (e.g., rising point, i.e., minimum point) on the waveform of a corresponding one of periodic pulses of the photoelectric pulse wave ("PPW") that are detected by the probe 38, as illustrated in FIG. 3. The PPW-relating-information obtaining means 74 iteratively calculates a PWP velocity $V_M$ (m/sec) of a pulse wave propagated through an artery of the patient, based on the calculated PPW time $DT_{RP}$, according to the following expression (1) pre-stored in the ROM 31:

$$V_M = L/(DT_{RP} - T_{PEP}) \quad (1)$$

where L (m) is a length of the artery as measured from the left ventricle to the position where the probe 38 is set, via the aorta; and $T_{PEP}$ (sec) is a pre-ejection period between the R-wave of the waveform of each pulse of the ECG pulse wave and the minimum point of the waveform of a corresponding pulse of an aortic pulse wave.

The values L, $T_{PEP}$ are constants, and are experimentally obtained in advance.

An index-value calculating means or circuit 76 calculates, based on the BP values measured in the last or current BP measuring operation of the BP measuring means 70, an index value Ia indicative of a hardness of a blood vessel of the patient. More specifically described, the index-value calculating means 76 calculates a pulse pressure $P_M$ by subtracting the measured diastolic BP value $BP_{DIA}$ from the measured systolic BP value $BP_{SYS}$, and calculates the index value $I_a$ by dividing the pulse pressure $P_M$ by the measured mean BP value $BP_{MEAN}$ (i.e. $I_a = P_M/BP_{MEAN}$). Meanwhile, it is known that as the arterial vessel becomes harder, the PWP velocity value $V_M$ becomes greater and the PWP time value $DT_{RP}$ becomes smaller. Accordingly, the index-value calculating means 76 may calculate an index value $I_a$ by dividing the PWP velocity value $V_M$, or the inverse of the PWP time value $DT_{RP}$, by a BP value measured by the BP measuring means 70 (e.g., measured systolic, mean, or diastolic BP value $BP_{SYS}$, $BP_{MEAN}$, $BP_{DIA}$) (i.e., $I_a = V_M/BP$, or $I_a = (1/DT_{RP})/BP$). As far as the present embodiment is concerned, the blood vessel means an arterial vessel such as an aorta, a brachial artery of an upper arm around which the cuff 10 is wrapped, or a big artery between the heart and the peripheral body portion on which the probe 38 is set.

A relationship determining means or circuit 78 determines two coefficients α, β in the following second or third linear expression (2) or (3), based on the systolic BP value $BP_{SYS}$ measured by the BP measuring means 70, and the PWP time value $DT_{RP}$ or the PWP velocity value $V_M$ calculated by the PPW-relating-information obtaining means 74. Each value $DT_{RP}$, $V_M$ may be an average of several values $DT_{RP}$, $V_M$ which are obtained immediately before each BP measurement. The above two linear expressions (2), (3) generally define a linear relationship between PWP time value $DT_{RP}$ and estimated BP value EBP, and a linear relationship between PWP velocity value $V_M$ and estimated BP value EBP, respectively. In place of the above-indicated relationship between estimated systolic BP value $EBP_{SYS}$ and either one of PWP time value $DT_{RP}$ and PWP velocity value $V_M$, a relationship between estimated mean or diastolic BP value $EBP_{MEAN}$, $EBP_{DIA}$ and either one of PWP time value $DT_{RP}$ and PWP velocity value $V_M$ may be employed. In short, a particular relationship between PWP-relating information and estimated BP value EBP may be determined depending upon which one of systolic, mean, and diastolic BP value is selected as estimated BP value EBP, i.e., monitored BP value.

$$EBP = \alpha(DT_{RP}) + \beta \quad (2)$$

where α is a negative constant and β is a positive constant.

$$EBP = \alpha(V_M) + \beta \quad (3)$$

where α and α are positive constants.

Figure 4:
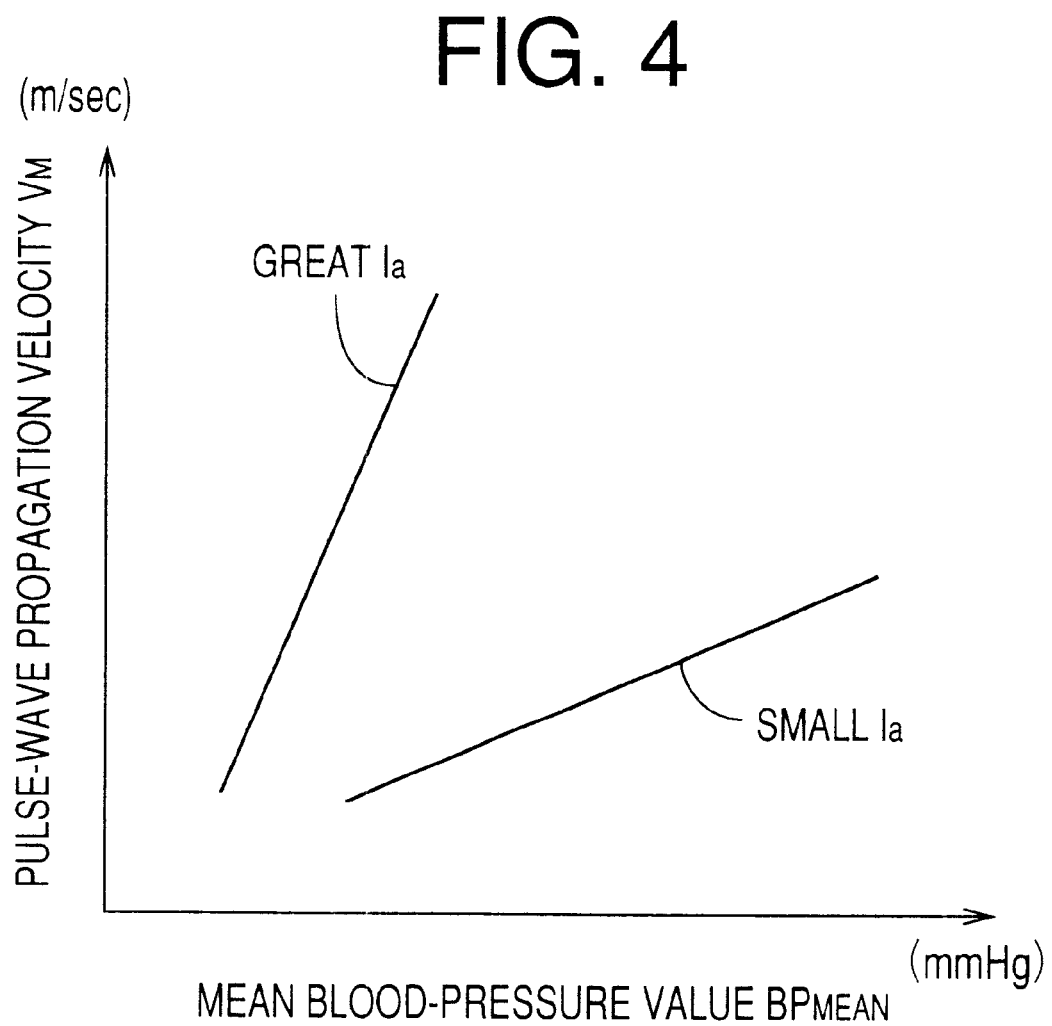
FIG. 4 is a view for illustrating two different relationships between pulse-wave-propagation velocity $V_M$ and mean blood-pressure value $BP_{MEAN}$ corresponding to two different index values $I_a$.

The linear relationship between PWP-relating information and estimated BP value EBP, represented by the linear expression (2) or (3), is based on the fact that the PWP-relating information relating to the pulse wave propagating through the arterial vessel changes in relation to the change of BP of the patient. However, the PWP-relating information also changes in relation to the hardness of the arterial vessel through which the pulse wave propagates. FIG. 4 shows a graph representing two different relationships between PWP velocity $V_M$ and mean BP value $BP_{MEAN}$ corresponding to two different (i.e., great and small) index values $I_a$. The graph shows that different index values $I_a$ indicate different relationships between PWP velocity $V_M$ and mean BP value $BP_{MEAN}$, respectively. Thus, in the present BP monitoring apparatus 8, the relationship determining means 78 determines a relationship between PWP-relating information and estimated BP value EBP, based on the BP value BP measured by the BP measuring means 70, the PWP time value $DT_{RP}$ or the PWP velocity value $V_M$ calculated by the PPW-relating-information obtaining means 74, and the index value Ia calculated by the index-value calculating means or circuit 76.

More specifically described, the relationship determining means 78 includes a slope determining means or circuit 80 which determines a slope α of the linear expression (2) or (3) based on the index value $I_a$ calculated by the index-value calculating means 76; and an intercept determining means or circuit 82 which determines an intercept β of the linear expression (2) or (3) based on the BP value BP measured by the BP measuring means 70, the PWP time value $DT_{RP}$ or the PWP velocity value $V_M$ calculated by the PPW-relating-information obtaining means 74, and the slope α determined by the slope determining means 80.

For example, the slope determining means 80 determines the slope α of the linear expression (2) or (3), based on the index value $I_a$ calculated by the index-value calculating means 76, according to the following fourth expression (4) pre-stored in the ROM 31:

$$\alpha = k \times I_a + c \quad (4)$$

where k is a positive constant, and c is a constant.

The pair of constants k, c are experimentally obtained in advance and are used for all patients. However, different pairs of constants k, c may be obtained in advance and used for different patients, or different diseases, respectively.

An estimated-BP ("EBP") determining means or circuit 84 iteratively determines an estimated BP value EBP of the patient, based on either one of an actual PWP time value $DT_{RP}$ and an actual PWP velocity value $V_M$ iteratively obtained by the PWP-relating-information obtaining means 74, according to the relationship represented by the second or third expression (2) or (3).

Figure 5:
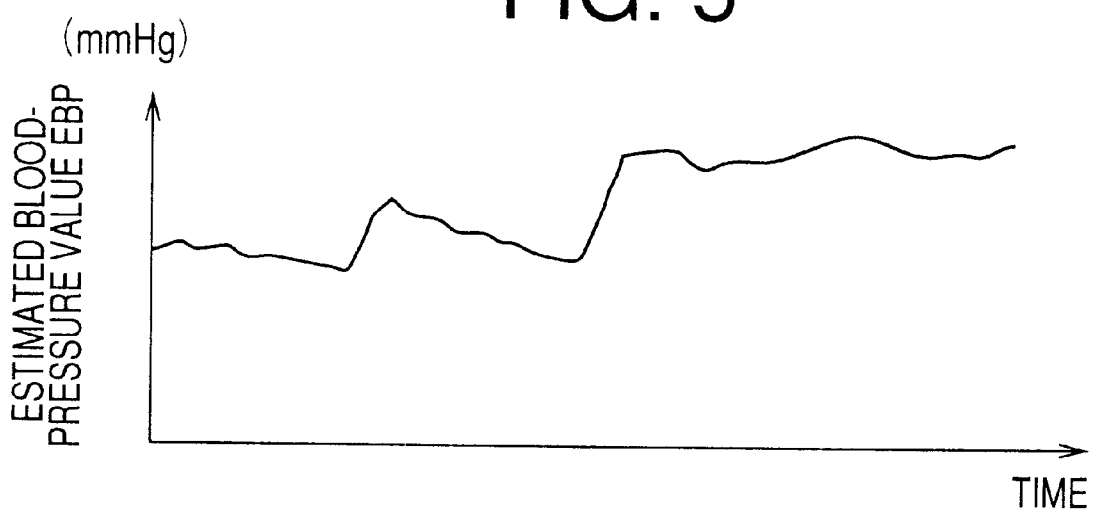
FIG. 5 is a view for illustrating a trend graph of estimated BP values EBP that is displayed by a display device of the apparatus of FIG. 1.

The control device 28 controls a display device 32 to display a trend graph of the estimated BP values EBP along a horizontal axis indicative of time, as shown in FIG. 5, so that the trend graph can be observed by a medical person, such as a doctor or a nurse, who attends to the patient.

A BP-measurement starting means or circuit 86 starts a BP measurement of the BP measuring means 70, when the absolute value of at least one value based on at least one estimated BP value EBP is not smaller than a reference (i.e., alarm) value. For example, the BP-measurement starting means 86 may start a BP measurement of the BP measuring means 70, when the respective absolute values of not less than twenty successive values based on not less than twenty successive estimated BP values EBP are not smaller than the alarm value. A value based on each estimated BP value EBP may be the each value EBP itself, a moving average of several values EBP including the each value EBP, or a change value that is an amount of change of the each value EBP from a "control" value EBP determined at the time of the last BP measuring operation, or the ratio of the amount of change to the "control" value EBP. More specifically described, the BP-measurement starting means 86 includes an EBP-abnormality judging means or circuit which judges that each estimated BP value EBP determined by the EBP determining means 78 is abnormal when at least one value based on at least one value EBP including the each value EBP does not fall within a reference (i.e., alarm) range. When the EBP-abnormality judging means judges that an estimated BP value EBP is abnormal, the BP-measurement starting means 86 starts a BP measurement of the BP measuring means 70.

Next, there will be described the operation of the control device 28 of the BP monitoring apparatus 8 by reference to the flow chart of FIG. 6 that represents the BP monitoring routine.

Figure 6:
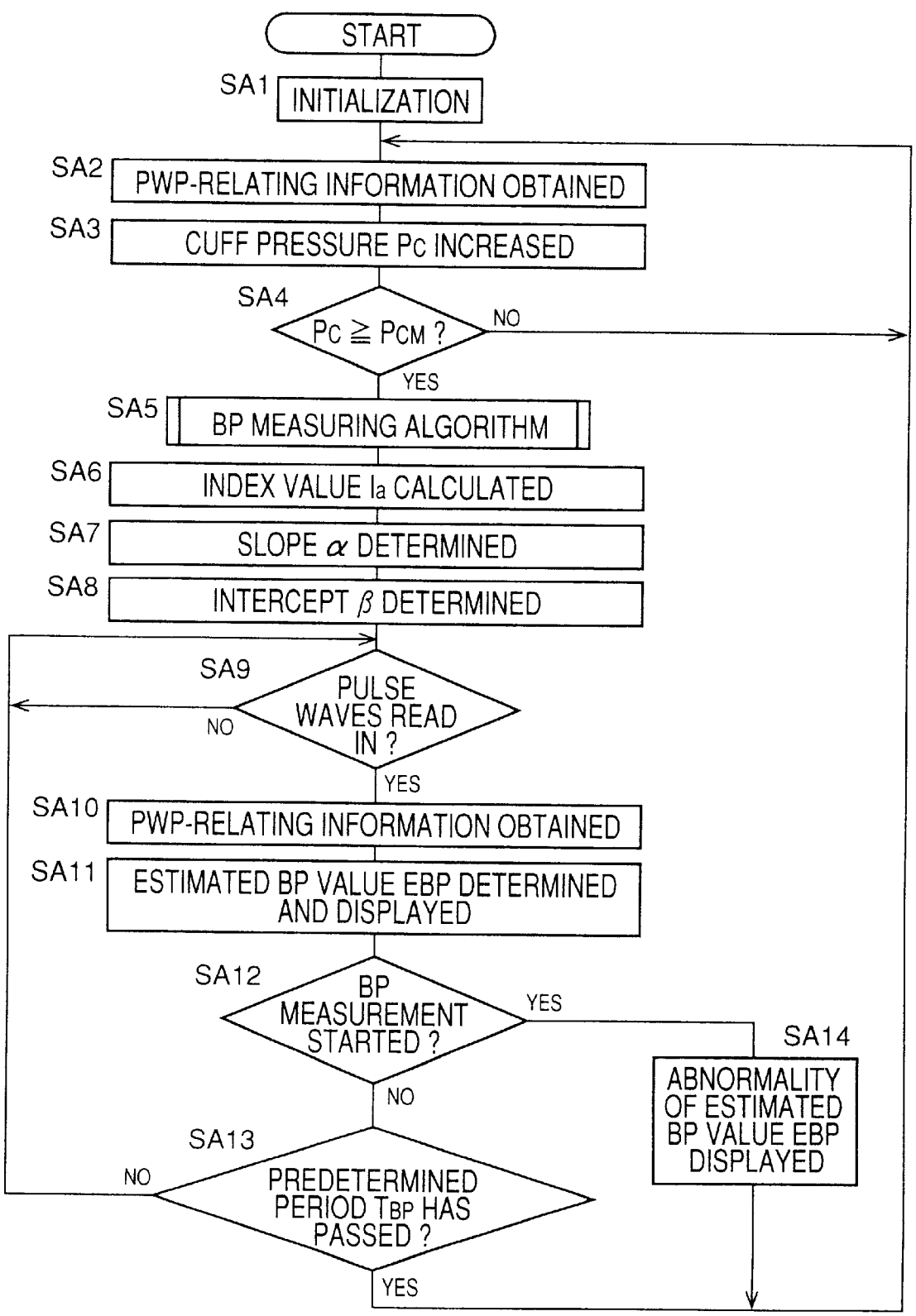
FIG. 6 is a flow chart representing a control program according to which the control device of the apparatus of FIG. 1 is operated for monitoring the BP of a living subject.

The control of the CPU 29 begins with Step SA1 of the flow chart of FIG. 6, where counters and registers (not shown) are reset, that is, the initialization of the control device 28 is carried out. Step SA1 is followed by Step SA2 to calculate, as a PWP time value $DT_{RP}$, a time difference between a R-wave of the waveform of a heartbeat-synchronous pulse of the ECG pulse wave and a rising point of the waveform of a corresponding pulse of the photoelectric pulse wave ("PPW") which are obtained immediately before the increasing of the cuff pressure. In addition, the CPU 29 calculates a PWP velocity value $V_M$ based on the calculated PWP time value $DT_{RP}$ according to the first expression (1). Step SA2 corresponds to the PWP-relating-information obtaining means 74.

The control of the CPU 29 goes to Steps SA3 and SA4 corresponding to the cuff-pressure control means 72. At Step SA3, the CPU 29 quickly increases the cuff pressure PC for a BP measurement of the BP measuring means 70, by switching the selector valve 16 to the inflation position and operating the air pump 18. Step SA3 is followed by Step SA4 to judge whether the cuff pressure $P_C$ is equal to or greater than a predetermined target pressure value $P_{CM}$ (e.g., 180 mmHg). If a negative judgement is made at Step SA4, the control of the CPU 29 goes back to Step SA2 so as to continue increasing the cuff pressure PC.

If a positive judgement is made at Step SA4, the control of the CPU 29 goes to Step SA5 to carry out a BP measuring algorithm. More specifically described, the air pump 18 is stopped and the selector value 16 is switched to the slow-deflation position where the valve 16 permits the pressurized air to be slowly discharged from the cuff 10. A systolic BP value $BP_{SYS}$, a mean BP value $BP_{MEAN}$, and a diastolic BP value $BP_{DIA}$ are determined, according to a well known oscillometric BP determining algorithm, based on the variation of respective amplitudes of heartbeat-synchronous pulses of the pulse wave represented by the cuff-pulse-wave signal $SM_1$ obtained while the cuff pressure $P_C$ is slowly decreased at a predetermined rate of about 3 mmHg/sec, and a heart rate value HR is determined based on the interval between two successive pulses of the pulse wave. The thus measured BP values and heart rate HR are displayed on the display device 32, and the selector valve 16 is switched to the quick-deflation position where the valve 16 permits the pressurized air to be quickly discharged from the cuff 10. Step SA5 corresponds to the BP measuring means 70.

Step SA5 is followed by Step SA6 corresponding to the index-value calculating means 76. At Step SA6, the CPU 29 calculates an index value $I_a$ indicative of a hardness of a blood vessel of the patient, based on the systolic, mean, and diastolic BP values $BP_{SYS}$, $BP_{MEAN}$, $BP_{DIA}$ measured at Step SA5. More specifically described, the CPU 29 calculates a pulse pressure $P_M$ by subtracting the measured diastolic BP value $BP_{DIA}$ from the measured systolic BP value $BP_{SYS}$, and calculates the index value Ia by dividing the pulse pressure $P_M$ by the measured mean BP value $BP_{MEAN}$ ($I_a = P_M / BP_{MEAN}$).

Step SA6 is followed by Steps SA7 and SA8 corresponding to the relationship determining means 78. At Step SA7 corresponding to the slope determining means 80, the CPU 29 calculates a slope α of the second or third expression (2) or (3), based on the index value $I_a$ calculated at Step SA6, according to the fourth expression (4).

At Step SA8 corresponding to the intercept determining means 82, the CPU 29 calculates an intercept β of the second or third expression (2) or (3), based on the BP value (e.g., systolic BP value $BP_{SYS}$) measured at Step SA5, the PWP-relating information obtained when the BP value is measured, i.e., calculated at Step SA2, and the slope α determined at Step SA7. After the linear relationship between PWP-relating information and estimated BP value EBP is thus determined, the control of the CPU 29 goes to Step SA9.

At Step SA9, the CPU 29 judges whether an R-wave of the waveform of a heartbeat-synchronous pulse of the ECG pulse wave and a rising point of the waveform of a corresponding pulse of the PPW have been read in. If a negative judgment is made at Step SA9, the control of the CPU 29 waits until a positive judgment is made at Step SA9. On the other hand, if a positive judgment is made at Step SA9, the control of the CPU 29 goes to Step SA10 corresponding to the PWP-relating-information obtaining means 74. At Step SA10, the CPU 29 calculates a PWP time value $DT_{RP}$, and a PWP velocity value $V_M$, based on the respective pulses of the ECG pulse wave and the PPW newly input at Step SA9, in the same manner as that employed at Step SA2.

Step SA10 is followed by Step SA11 where the CPU 29 determines an estimated (systolic, mean, or diastolic) BP value EBP, based on the PWP time value $DT_{RP}$ or the PWP velocity $V_M$ calculated at Step SA10, according to the linear relationship between PWP-relating information and estimated BP value EBP determined at Steps SA7 and SA8. In addition, the CPU 29 controls the display device 32 to display, as shown in FIG. 5, a trend graph of estimated BP values EBP including the thus determined, "current" value EBP. Step SA11 corresponding to the EBP determining means 84.

Step SA11 is followed by Step SA12 corresponding to the BP-measurement starting means 86. At Step SA13, the CPU 29 starts a BP measurement of the BP measuring means 70, when the "current" estimated BP value EBP is judged as being abnormal. For instance, the CPU 29 judges that the estimated BP value EBP determined at Step SA11 is abnormal when the state in which the estimated BP value EBP determined in each control cycle falls outside a predetermined alarm range has continued for a time period corresponding to not less than a predetermined number of pulses (e.g., 20 pulses).

If a negative judgment is made at Step SA12, the control of the CPU 29 goes to Step SA13. At Step SA13, the CPU 29 judges whether a predetermined period (e.g., 20 minutes), that is, a calibration period, has passed after the last BP measuring operation has been carried out using the inflatable cuff 10 at Step SA5. If a negative judgment is made at Step SA13, the control of the CPU 29 goes back to Step SA9 and the following steps so as to carry out a BP monitoring control cycle, i.e., successively or continuously determine an estimated BP value EBP based on each of successive heartbeat-synchronous pulses of the ECG pulse wave and the PPW. The display device 32 displays the trend graph of the thus determined values EBP. On the other hand, if a positive judgment is made at Step SA12, the control of the CPU 29 goes back to Step SA2 and the following steps so as to carry out a calibration control cycle, i.e., determine a new relationship between PWP-relating information and estimated BP value EBP.

Meanwhile, if a positive judgment is made at Step SA12, the control of the CPU 29 goes to Step SA14. At Step SA14, the CPU 29 controls the display device 32 to display a symbol or a message indicating the abnormality of the "current" estimated BP value EBP. Then, the control of the CPU 29 goes back to Step SA2 and the following steps so as to start a BP measurement using the cuff 10 and determine a new relationship between PWP-relating information and estimated BP value EBP.

It is apparent from the foregoing description that in the present embodiment, the index-value calculating means 76 calculates the index value $I_a$ indicative of the hardness of the blood vessel of the patient based on the BP values measured by the BP measuring means 70, the slope determining means 80 determines the slope $\alpha$ of the second or third expression (2) or (3) based on the index value $I_a$ calculated by the index-value calculating means 76, and the intercept determining means 82 determines the intercept $\beta$ of the second or third expression (2) or (3), based on the BP value measured by the BP measuring means 70, the PWP-relating information obtained when the BP value is measured by the BP measuring means 70, and the slope $\alpha$ determined by the slope determining means 80. Thus, the present BP monitoring apparatus 8 can determine a relationship between PWP-relating information and estimated BP value EBP, only with a single BP measuring operation of the BP measuring means or device 70.

Next, there will be described a second embodiment of the present invention by reference to FIGS. 7 to 9. The second embodiment also relates to a BP monitoring apparatus which may have the same hardware construction as that of the apparatus 8 shown in FIG. 1. However, the second BP monitoring apparatus is operated according to a different software control program represented by the flow chart of FIG. 9. The same reference numerals as used for the first BP monitoring apparatus 8 are used to designate the corresponding elements and parts of the second BP monitoring apparatus, and the description thereof is omitted.

Figure 7:
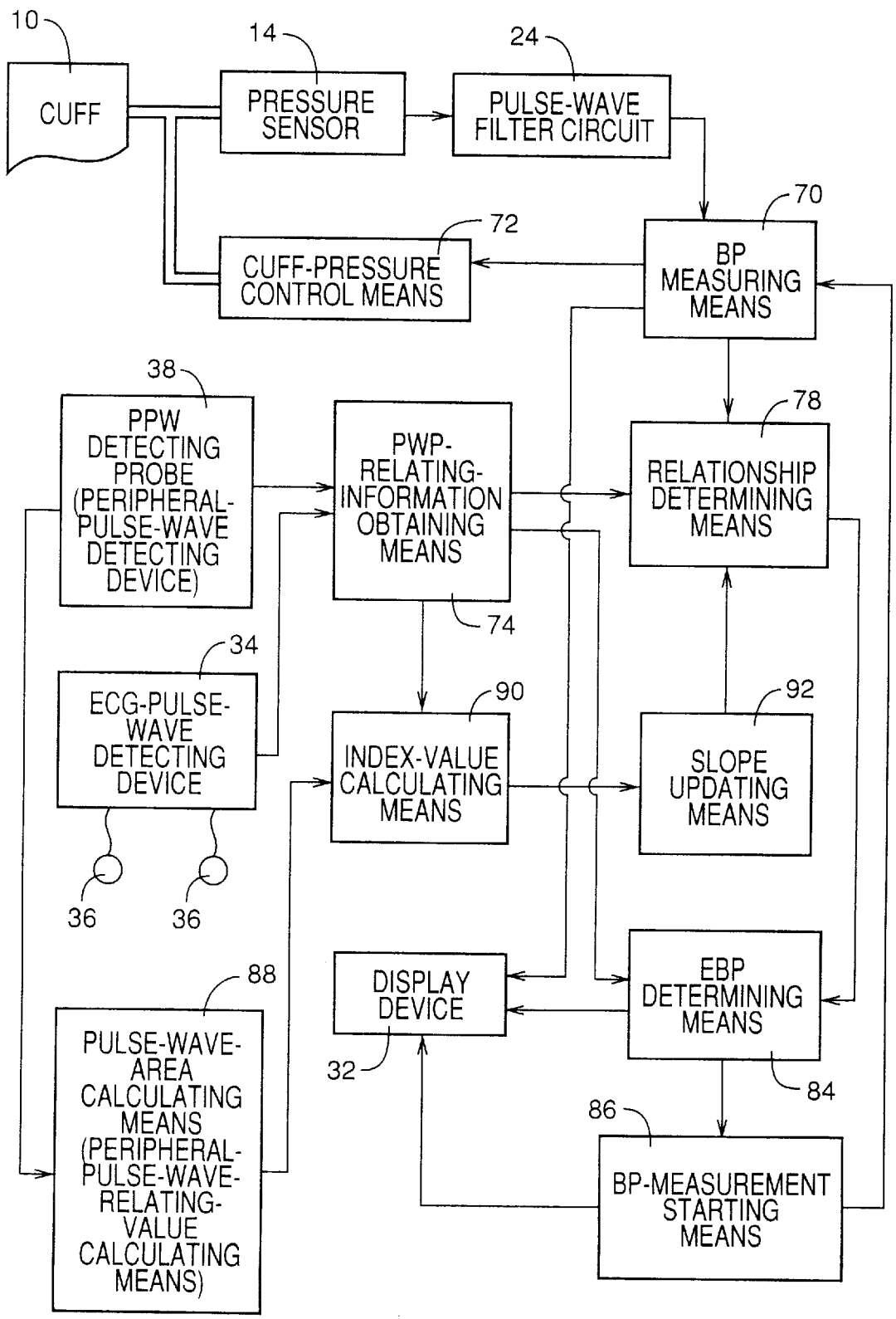
FIG. 7 is a block diagram corresponding to FIG. 2, for illustrating essential functions of an electronic control device of another BP monitoring apparatus as a second embodiment of the present invention.

FIG. 7 illustrates essential functions of an electronic control device 28 of the second BP monitoring apparatus.

A pulse-wave-area calculating means or circuit 88 functions as a peripheral-pulse-wave-relating-value calculating means which iteratively calculates a value relating to a peripheral pulse wave obtained from the patient. More specifically described, the pulse-wave-area calculating means 88 iteratively calculates a pulse-wave area value VR by normalizing an area S defined or enveloped by the waveform of each heartbeat-synchronous pulse of a photoelectric pulse wave ("PPW") detected by a PPW detecting probe 38, based on a period W and an amplitude L of the each pulse. As shown in FIG. 8, the waveform of each pulse of the PPW is defined by a series of data points indicative of respective magnitudes which are input at a predetermined short interval such as several milliseconds to several tens of milliseconds. The pulse-wave area S $(=S_1+S_2)$ is obtained by integrating, over the period W of the each pulse, respective magnitudes of the data points of the each pulse, and then a normalized pulse-wave area value VR is obtained according to the following expression: VR=S/(W×L). The normalized pulse-wave area value VR is a dimensionless value indicative of the ratio of the pulse-wave area S to a rectangular area defined by the period W and the amplitude L of the each pulse. For this parameter, the symbol "%MAP" may be used in place of the symbol "VR".

An index-value calculating means or circuit 90 iteratively calculates an index value Ia indicative of a hardness of a blood vessel of the patient, based on each normalized pulse-wave area value VR iteratively calculated by the pulse-wave-area calculating means 88. The normalized pulse-wave area value VR changes in relation with the change of BP of the patient. Hence, for example, the index-value calculating means 90 may calculate an index value $I_a$ by dividing each PWP velocity value $V_M$, or the inverse of each PWP time value $DT_{RP}$, iteratively calculated by a PWP-relating information obtaining means 74, by each normalized pulse-wave area value VR iteratively calculated by the pulse-wave-area calculating means 88 (i.e., $I_a=V_M/V_R$, or $I_a=(1/DT_{RP})/VR$).

A slope updating means or circuit 92 iteratively determines, based on each index value $I_a$ iteratively calculated by the index-value calculating means 90, a new slope $\alpha$ of the second or third expression (2) or (3) each of which defines a relationship between PWP-relating information and estimated BP value EBP, and updates the current $\alpha$ of the expression (2), (3) by replacing the current $\alpha$ with the determined new slope $\alpha$. For example, the slope updating means 92 determines a new slope $\alpha$ of the expression (2), (3), based on each index value $I_a$ calculated by the index-value calculating means 90, according to the following fifth expression (5), pre-stored in the ROM 31, which defines a relationship between index value Ia and slope (or coefficient) α:

$$\alpha = k' \times I_a + c' \qquad (5)$$

where k' is a positive constant, and c' is a constant.

The pair of constants k', c' are experimentally obtained in advance and are used for all patients. However, different pairs of constants k, c may be obtained in advance and used for different individual patients, or different diseases, respectively.

A relationship determining means or circuit 78 of the second BP monitoring apparatus is identical with the relationship determining means or circuit 78 employed in the first BP monitoring apparatus 8 of FIG. 2, i.e., includes the slope determining means 80 and the intercept determining means 82 and determine a relationship between PWP-relating information and estimated BP value EBP based on a single (systolic, mean, or diastolic) BP value measured by the BP measuring means 70, a single piece of PWP-relating information obtained by the PWP-relating information obtaining means 74 when the BP value is measured by the BP measuring means 70, and an index value $I_a$ calculated by the index-value calculating means 76 of FIG. 2.

However, the relationship determining means 78 of the second BP monitoring apparatus may be different from the relationship determining means 78 of FIG. 2, for example, may be a conventional one which determines a relationship between PWP-relating information and estimated BP value EBP based on two (systolic, mean, or diastolic) BP values measured by the BP measuring means 70 at different times and two pieces of PWP-relating information obtained by the PWP-relating information obtaining means 74 when the two BP values are measured by the BP measuring means 70, respectively.

Next, there will be described the operation of the control device 28 of the second BP monitoring apparatus by reference to the flow chart of FIG. 9 that represents the BP monitoring routine.

Steps SB1 to SB5 of FIG. 9 are identical with Steps SA1 to SA5 of FIG. 6, respectively. Thus, a systolic, a mean, and a diastolic BP value of the patient is measured.

Step SB5 is followed by Step SB6 corresponding to the relationship determining means 78. At Step SB6, a CPU 29 of the control device 28 determines a linear relationship between PWP-relating information (PWP time value $DT_{RP}$ or PWP velocity $V_M$) and estimated BP value EBP (estimated systolic, mean, or diastolic BP value), i.e., the second or third linear expression (2) or (3), in an appropriate one of the above-described manners.

After the linear relationship between PWP-relating information and estimated BP value EBP is thus determined, the control of the CPU 29 goes to Step SB7.

At Step SB7, the CPU 29 judges whether an R-wave of the waveform of a heartbeat-synchronous pulse of an electrocardiographic ("ECG") pulse wave and a rising point of the waveform of a corresponding pulse of a photoelectric pulse wave ("PPW") have been read in through an ECG-pulse-wave detecting device 34 and a PPW detecting probe 38. If a negative judgment is made at Step SB7, the control of the CPU 29 waits until a positive judgment is made at Step SB7. On the other hand, if a positive judgment is made at Step SB7, the control of the CPU 29 goes to Step SB8 corresponding to the pulse-wave-area calculating means 88. At Step SB8, the CPU 29 calculates a normalized pulse-wave area value VR, based on the waveform of a heartbeat-synchronous pulse of the PPW newly input at Step SB7.

Next, the control of the CPU 29 goes to Step SB9 corresponding to the PWP-relating-information obtaining means 74. At Step SB9, the CPU 29 calculates a PWP time value $DT_{RP}$, and a PWP velocity value $V_M$, based on the respective pulses of the ECG pulse wave and the PPW newly input at Step SB7, in the same manner as that employed at Step SB2.

Step SB9 is followed by Step SB10 corresponding to the index-value calculating means 90. At Step SB10, the CPU 29 calculate an index value $I_a$ by dividing the PWP velocity value $V_M$ or the inverse ($1/DT_{RP}$) of the PWP time value $DT_{RP}$, calculated at Step SB9, by the normalized pulse-wave area value VR calculated at Step SB10 (i.e., $I_a = V_M/VR$, or $I_a (1/DT_{RP})/VR$).

Step SB10 is followed by Step SB11 to determine a new slope α of the expression (2), (3) determined at Step SB, or at Step SB11 in the prior control cycle, based on the index value $I_a$ calculated at Step SB10 in the current control cycle, according to the fifth expression (5), and update the current slope α of the expression (2), (3) by replacing the current slope α with the thus determined new slope α.

Steps SB12 to SB15 are identical with Steps SA11 to SA14, respectively. In short, an estimated BP value EBP is determined according to the expression (2), (3) the slope α of which has been updated at Step SB11, and is displayed on a display device 32. In addition, the thus determined estimated BP value EBP is used in judging, at Step SB13, whether or not to start a BP measurement of the BP measuring means 70.

It emerges from the foregoing description that in the second BP monitoring apparatus, the pulse-wave-area calculating means 88 iteratively calculates a normalized pulse-wave area value VR based on each of successive heartbeat-synchronous pulses of the PPW detected by the probe 38, and the index-value calculating means 90 iteratively calculates an index value $I_a$ based on each normalized pulse-wave area value VR calculated by the pulse-wave-area calculating means 88. Then, the slope updating means 92 iteratively updates the slope α of the second or third expression (2) or (3) based on each index value Ia calculated by the index-value calculating means 90. Therefore, the accuracy of the relationship between PWP-relating information and estimated BP value EBP, defined by the expression (2), (3), is maintained throughout the monitoring of BP of the patient.

While the present invention has been described in its preferred embodiments, it is to be understood that the present invention may be otherwise embodied.

For example, in each of the illustrated embodiments, the reflection-type PWP detecting probe 38 as part of the pulse oximeter is utilized as the peripheral-pulse-wave detecting device. However, the probe 38 may be replaced with an appropriate one selected from other sorts of pulse-wave sensors including a pressure-pulse-wave sensor which detects a pressure pulse wave by being pressed on a radial artery of a living subject; an impedance-pulse-wave sensor which detects an impedance pulse wave through electrodes being put on a body portion (e.g., a finger or an arm) of a subject; or a transmission-type PWP sensor which detects a PWP from the light transmitted through a body portion (e.g., a finger) of a subject.

In each of the illustrated embodiments, the pulse-wave-area calculating means 88 functions as the peripheral-pulse-wave-relating-value calculating means, and the normalized pulse-wave area value VR is calculated as the value relating to the peripheral pulse wave obtained from the peripheral body portion (e.g., finger) of the patient. However, the normalized pulse-wave area value VR may be replaced with a value which is obtained by normalizing a first half area $S_1$, or a second half area $S_2$, of the total area S of the waveform of each pulse of the PPW signal $SM_3$ (FIG. 8). The total area S is divided into the two half areas $S_1$, $S_2$, with a vertical line passing the upper peak (i.e., maximum) point of the waveform of the each pulse. The first half area $S_1$ may be normalized by dividing the area $S_1$ by a rectangular area defined by an amplitude L and a first half time duration $W_1$ between a left-hand end time point of each pulse and an intermediate time point corresponding to the upper peak, and the second half area $S_2$ may be normalized by dividing the area $S_2$ by a rectangular area defined by the amplitude L and a second half time duration $W_2$ between the other, right-hand end point and the intermediate time point.

Alternatively, the normalized pulse-wave area value VR may be replaced with a value which is obtained by normalizing a width Z of the waveform of each pulse as measured at a height equal to two thirds of the amplitude L. The width Z may be normalized by dividing the width Z by the amplitude L, or a pulse period W. Otherwise, the normalized pulse-wave area value VR may be replaced with any value relating to a total or half area of the waveform of each pulse of the PPW, or any value indicative of a degree of upward sharpness of the waveform of each pulse.

In the second BP monitoring apparatus shown in FIGS. 7 to 9, the slope $\alpha$ of the expression (2), (3) is updated based on each index value $I_a$ which is successively calculated based on each normalized pulse-wave area value VR which in turn is successively calculated based on the waveform of each heartbeat-synchronous pulse of the PPW. That is, the slope $\alpha$ is updated in response to every heartbeat-synchronous pulse of the PPW. However, the slope $\alpha$ may be updated in response to every second or third pulse of the PPW, or at a regular short time interval of, e.g., from several seconds to several tens of seconds.

It is to be understood that the present invention may be embodied with other changes, improvements, and modifications that may occur to one having skill in the art without departing from the spirit and scope of the invention defined in the appended claims.

What is claimed is:

1. A blood-pressure monitoring apparatus comprising:
   a measuring device which includes an inflatable cuff adapted to apply a pressing pressure to a body portion of a living subject and which measures at least one blood-pressure value of the living subject by changing the pressing pressure of the inflatable cuff;
   a pulse-wave-propagation-relating-information obtaining device which iteratively obtains a piece of pulse-wave-propagation-relating information relating to propagation of a pulse wave through an arterial vessel of the living subject;
   estimating means for iteratively estimating a blood-pressure value, EBP, of the living subject, based on each piece of pulse-wave-propagation-relating information, PWPI, obtained by the pulse-wave-propagation-relating-information obtaining device, according to a linear relationship between pulse-wave-propagation-relating information and blood pressure, the linear relationship being defined by a following linear expression, EBP=$\alpha$(PWPI)+$\beta$, where $\alpha$ is a slope and $\beta$ is an intercept;
   index-value calculating means for calculating, based on the blood-pressure value of the living subject measured by the measuring device, an index value indicative of a hardness of a blood vessel of the living subject;
   slope determining means for determining, based on the calculated index value, the slope $\alpha$ of the linear expression; and
   intercept determining means for determining the intercept $\beta$ of the linear expression, based on the blood-pressure value measured by the measuring device, the piece of pulse-wave-propagation-relating information obtained by the pulse-wave-propagation-relating-information obtaining device when the blood-pressure value is measured by the measuring device, and the slope $\alpha$ determined by the slope determining means.

2. A blood-pressure monitoring apparatus comprising:
   a measuring device which includes an inflatable cuff adapted to apply a pressing pressure to a first body portion of a living subject and which measures at least one blood-pressure value of the living subject by changing the pressing pressure of the inflatable cuff;
   a pulse-wave-propagation-relating-information obtaining device which iteratively obtains a piece of pulse-wave-propagation-relating information relating to propagation of a pulse wave through an arterial vessel of the living subject;
   estimating means for iteratively estimating a blood-pressure value, EBP, of the living subject, based on each piece of pulse-wave-propagation-relating information, PWPI, obtained by the pulse-wave-propagation-relating-information obtaining device, according to a linear relationship between pulse-wave-propagation-relating information and blood pressure, the linear relationship being defined by a following linear expression, EBP=$\alpha$(PWPI)+$\beta$, where $\alpha$ is a slope and $\beta$ is an intercept;
   a pulse-wave detecting device which detects a peripheral pulse wave including a plurality of heartbeat-synchronous pulses, from a second body portion of the living subject;
   peripheral-pulse-wave-relating-value calculating means for iteratively calculating a peripheral-pulse-wave-relating value relating to each of the heartbeat-synchronous pulses of the peripheral pulse wave detected by the pulse-wave detecting device;
   index-value calculating means for iteratively calculating, based on each of the iteratively calculated peripheral-pulse-wave-relating values, an index value indicative of a hardness of a blood vessel of the living subject; and
   slope updating means for iteratively determining, based on each of the iteratively calculated index values, a new slope $\alpha$ for the linear expression, and updating a current slope $\alpha$ of the linear expression by replacing the current slope $\alpha$ with the determined new slope $\alpha$.

3. A blood-pressure monitoring apparatus comprising:
   a measuring device which includes an inflatable cuff adapted to apply a pressing pressure to a first body portion of a living subject and which measures at least one blood-pressure value of the living subject by changing the pressing pressure of the inflatable cuff;
   a pulse-wave-propagation-relating-information obtaining device which iteratively obtains a piece of pulse-wave-propagation-relating information relating to propagation of a pulse wave through an arterial vessel of the living subject;
   estimating means for iteratively estimating a blood-pressure value, EBP, of the living subject, based on each piece of pulse-wave-propagation-relating information, PWPI, obtained by the pulse-wave-propagation-relating-information obtaining device, according to a linear relationship between pulse-wave-propagation-relating information and blood pressure, the linear relationship being defined by a following linear expression, $EBP=\alpha(PWPI)+\beta$, where $\alpha$ is a slope and $\beta$ is an intercept;

index-value calculating means for calculating an index value indicative of a hardness of a blood vessel of the living subject; and slope determining means for determining, based on the calculated index value, the slope $\alpha$ of the linear expression.

4. An apparatus according to claim 3, further comprising intercept determining means for determining the intercept $\beta$ of the linear expression, based on the blood-pressure value measured by the measuring device, the piece of pulse-wave-propagation-relating information obtained by the pulse-wave-propagation-relating-information obtaining device when the blood-pressure value is measured by the measuring device, and the slope $\alpha$ determined by the slope determining means.

5. An apparatus according to claim 3, wherein the slope determining means comprises slope updating means for iteratively determining a new slope $\alpha$ for the linear expression, based on each of the iteratively calculated index values, and updating a current slope $\alpha$ of the linear expression by replacing the current slope $\alpha$ with the determined new slope $\alpha$.

6. An apparatus according to claim 3, wherein the pulse-wave-propagation-relating-information obtaining device comprises at least one of pulse-wave-propagation-time calculating means for iteratively calculating a pulse-wave propagation time which is needed for each of a plurality of heartbeat-synchronous pulses of the pulse wave to propagate between two portions of the arterial vessel of the living subject, and pulse-wave-propagation-velocity calculating means for iteratively calculating a pulse-wave propagation velocity at which each of a plurality of heartbeat-synchronous pulses of the pulse wave propagates between two portions of the arterial vessel of the living subject.

7. An apparatus according to claim 3, wherein the pulse-wave-propagation-relating-information obtaining device comprises an electrocardiographic-pulse-wave detecting device which includes a plurality of electrodes adapted to be put on a plurality of portions of the living body and detects an electrocardiographic pulse wave including a plurality of heartbeat-synchronous pulses, from the subject via the electrodes, and a photoelectric-pulse-wave detecting device which is adapted to be worn on a second body portion of the living subject, and which emits a light toward the second body portion and obtains a photoelectric pulse wave including a plurality of heartbeat-synchronous pulses, from the light received from the second body portion.

8. An apparatus according to claim 3, wherein the measuring device comprises means for measuring a systolic, a mean, and a diastolic blood-pressure value of the living subject by changing the pressing pressure of the inflatable cuff, and wherein the index-value calculating means comprises means for calculating a pulse pressure by subtracting the measured diastolic blood-pressure value from the measured systolic blood-pressure value, and calculating the index value by dividing the thus calculated pulse pressure by the measured mean blood-pressure value.

9. An apparatus according to claim 3, wherein the index-value calculating means comprises means for calculating, based on the blood-pressure value of the living subject measured by the measuring device, the index value indicative of the hardness of the blood vessel of the living subject.

10. An apparatus according to claim 9, further comprising:

intercept determining means for determining the intercept $\beta$ of the linear expression, based on the blood-pressure value measured by the measuring device, the piece of pulse-wave-propagation-relating information obtained by the pulse-wave-propagation-relating-information obtaining device when the blood-pressure value is measured by the measuring device, and the slope $\alpha$ determined by the slope determining means;

a pulse-wave detecting device which detects a peripheral pulse wave including a plurality of heartbeat-synchronous pulses, from a second body portion of the living subject;

peripheral-pulse-wave-relating-value calculating means for iteratively calculating a peripheral-pulse-wave-relating value relating to each of the heartbeat-synchronous pulses of the peripheral pulse wave detected by the pulse-wave detecting device;

the index-value calculating means comprising means for iteratively calculating, based on each of the iteratively calculated peripheral-pulse-wave-relating values, the index value indicative of the hardness of the blood vessel of the living subject; and the slope determining means comprising slope updating means for iteratively determining a new slope $\alpha$ for the linear expression, based on each of the iteratively calculated index values, and updating a current slope $\alpha$ of the linear expression by replacing the current slope $\alpha$ with the determined new slope $\alpha$.

11. An apparatus according to claim 3, further comprising:

a pulse-wave detecting device which detects a peripheral pulse wave including a plurality of heartbeat-synchronous pulses, from a second body portion of the living subject; and peripheral-pulse-wave-relating-value calculating means for iteratively calculating a peripheral-pulse-wave-relating value relating to each of the heartbeat-synchronous pulses of the peripheral pulse wave detected by the pulse-wave detecting device, wherein the index-value calculating means comprises means for iteratively calculating, based on each of the iteratively calculated peripheral-pulse-wave-relating values, the index value indicative of the hardness of the blood vessel of the living subject.

12. An apparatus according to claim 11, wherein the index-value calculating means comprises means for iteratively calculating the index value based on each piece of pulse-wave-propagation-relating information iteratively obtained by the pulse-wave-propagation-relating-information obtaining device and said each peripheral-pulse-wave-relating value iteratively calculated by the peripheral-pulse-wave-relating-value calculating means.

13. An apparatus according to claim 6, wherein the peripheral-pulse-wave-relating-value calculating means comprises means for iteratively calculating a value relating to an area defined by a waveform of said each heartbeat-synchronous pulse of the peripheral pulse wave detected by the pulse-wave detecting device.

14. An apparatus according to claim 3, wherein the index-value calculating means comprises means for calculating the index value based on the blood-pressure value measured by the measuring device and the piece of pulse-wave-propagation-relating information obtained by the pulse-wave-propagation-relating-information obtaining device when the blood-pressure value is measured by the measuring device.

15. An apparatus according to claim 3, wherein the slope determining means comprises means for determining the slope $\alpha$ of the linear expression based on the calculated index value, $I_a$, according to a following expression: $\alpha = k \times I_a + c$, where k and c are predetermined constants.

16. An apparatus according to claim 3, further comprising starting means for judging whether the blood-pressure value estimated by the estimating means is abnormal, and starting a blood-pressure measurement of the measuring device when the estimated blood-pressure value is judged as being abnormal.

* * * * *